(12) United States Patent
Warden et al.

(10) Patent No.: US 7,048,746 B2
(45) Date of Patent: May 23, 2006

(54) METHOD AND INSTRUMENT FOR THERMAL SUTURE CUTTING

(76) Inventors: Matthew P. Warden, 386 Commercial St., Apartment 4 C, Boston, MA (US) 02109; Michael A. Rolnick, 12533 Folley Quarter Rd., Ellicott City, MD (US) 21042; Robert A. Van Wyk, 10801 Starkey Rd. #104-16, Largo, FL (US) 33777

( * ) Notice: Subject to any disclaimer, the term of this patent is extended or adjusted under 35 U.S.C. 154(b) by 0 days.

(21) Appl. No.: 10/600,368

(22) Filed: Jun. 23, 2003

(65) Prior Publication Data

US 2004/0002717 A1    Jan. 1, 2004

Related U.S. Application Data

(60) Provisional application No. 60/391,887, filed on Jun. 27, 2002.

(51) Int. Cl.
*A61B 17/10* (2006.01)

(52) U.S. Cl. .......................... 606/138; 606/27; 606/28; 606/29; 606/30

(58) Field of Classification Search ................ 606/138, 606/139, 144, 148, 167, 27–31, 37, 39, 45, 606/46, 228; 607/96–99
See application file for complete search history.

(56) References Cited

U.S. PATENT DOCUMENTS

| | | | | |
|---|---|---|---|---|
| 3,234,356 A | * | 2/1966 | Babb | 606/30 |
| 4,384,406 A | * | 5/1983 | Tischlinger | 606/138 |
| 4,494,542 A | * | 1/1985 | Lee | 606/138 |
| 4,516,574 A | | 5/1985 | Hewes, Jr. | |
| 4,540,873 A | | 9/1985 | Kester | |
| 4,662,068 A | | 5/1987 | Polonsky | |
| 4,845,851 A | | 7/1989 | Warthen | |
| 5,452,513 A | | 9/1995 | Zinnbauer et al. | |
| 5,472,654 A | | 12/1995 | Crawford | |
| 5,565,122 A | | 10/1996 | Zinnbauer et al. | |
| 6,254,620 B1 | * | 7/2001 | Koh et al. | 606/167 |
| 6,733,509 B1 | * | 5/2004 | Nobles et al. | 606/138 |

* cited by examiner

*Primary Examiner*—Anhtuan T. Nguyen
*Assistant Examiner*—Michael Mendoza
(74) *Attorney, Agent, or Firm*—Chalin Smith; Smith Patent Consulting, LLC (57) ABSTRACT

Novel suture removal instrument and technique are described herein. The invention utilizes a newly designed thermal filament to allow the tip of the suture removal instrument to be slipped under the stitch in order to heat and cut the stitch. Current suture removal techniques utilize scissors, forceps, and/or scalpels. These techniques, which are well known in the art, are problematic because they exert tension on the stitch and are associated with patient discomfort. Small stitches add to the difficulty of suture removal because they have less suture laxity for scissor insertion. The present invention therefore allows for more rapid suture removal with less patient discomfort and at a competitive or lower cost.

16 Claims, 13 Drawing Sheets

METHOD AND INSTRUMENT FOR THERMAL SUTURE CUTTING

PRIORITY INFORMATION

This application claims the benefit of U.S. Provisional Application Ser. No. 60/391,887, filed Jun. 27, 2002, the content of which is incorporated by reference herein in its entirety.

TECHNICAL FIELD OF THE INVENTION

The present invention relates to the field of suture removal. More particularly, the present invention provides a method and instrument for thermally cutting a suture which minimizes the tension placed on the suture during removal, thereby reducing pain, bleeding and tissue disruption.

BACKGROUND OF THE INVENTION

Suture removal is an important part of wound repair in medicine. Internal sutures are absorbable so they are essentially "removed" by the body. External sutures or sutures on the surface of the body are nonabsorbable. Nonabsorbable sutures are advantageous, because they have a higher tensile strength than absorbable sutures. As such, they are the preferred suture for closure of external wounds. However, they carry with them the additional task of requiring manual suture removal.

The removal of sutures is problematic for many doctors. Current suture removal techniques utilize standard instruments to manipulate and cut a stitch. This technique requires considerable tension on, and manipulation of, the stitch. The resulting pain, bleeding, and tissue disruption are uncomfortable and anxiety provoking for the patient and compromise the cosmesis of the wound repair. Lastly, the technique is time consuming for the physician.

Current manual suture removal techniques rely on two methods. The first technique utilizes a suture removal kit containing a pair of forceps, scissors, and gauze pad. This technique consists of grasping the knot of the suture with the forceps and lifting the stitch enough to slip the scissors under the suture. The scissors then cut the stitch, which is then pulled out of the skin with the forceps. Unfortunately, the scissors generally have a blunt end, making it difficult to raise the stitch sufficiently off the skin to slip the distal tip of the scissors under the stitch. Additionally, the action of bringing the scissors blades together to cut the stitch creates significant tension on the suture. The gauze, included in the suture removal kit, is most aptly used to wipe away the blood which results from the manipulation necessary to remove the suture. The second current method for suture removal replaces the scissors with a thin knife but requires the same manipulation and results in similar tissue disruption and bleeding.

It is accordingly an object of this invention to provide a method and instrument for suture removal which produces less tension in the suture than current methods.

It is accordingly a further object of this invention to provide a method and instrument for suture removal which minimizes pain, bleeding and tissue disruption.

It is a further object of this invention to provide a method and instrument for suture removal which allows sutures to be removed in less time than currently available methods and devices.

SUMMARY OF THE INVENTION

The present invention provides a method and instrument for applying heat to the loop portion of a suture used to close a wound so as to melt the suture material, causing the loop to rupture. The cutting method disclosed and associated instrument allow the suture to be separated while producing less tension in the suture than current methods, thereby minimizing patient discomfort, tissue disruption and bleeding.

In a preferred method of the instant invention; a resistive heating element is brought into contact with the loop of a suture used to close a wound. The heating element is placed under the suture loop (or stitch), preferably between the patient's skin and a knotted portion of the suture. Power is supplied to the heating element for a brief time, during which the element heats and melts the suture in contact therewith, causing the loop to rupture. Thereafter the suture is removed in the usual manner, i.e., using forceps or the like to extract the remaining suture material.

Accordingly, the present invention provides a suture removal instrument comprising:
 (a) an elongated body having a proximal handle portion and insulated distal portion;
 (b) a first conductive member extending from the insulated distal portion of the elongated body, terminating in a tapered tip;
 (c) a resistive heating element extending alongside the first conductive member and affixed at its distal end to the tapered tip;
 (d) conduction means for supplying power to the heating element; and
 (e) activation means for controlling the supply of power to the heating element.

The elongated body may serve as a handle for the operator to grasp and/or as a housing for the operating components, such as the power source, conduction means and activation means. The elongated body may be formed from any suitable medical-grade material, such as plastic, metal, polycarbonate, polyvinyl chloride, and the like. In a preferred embodiment, the elongated body comprises a cylindrical housing.

Figure 12:
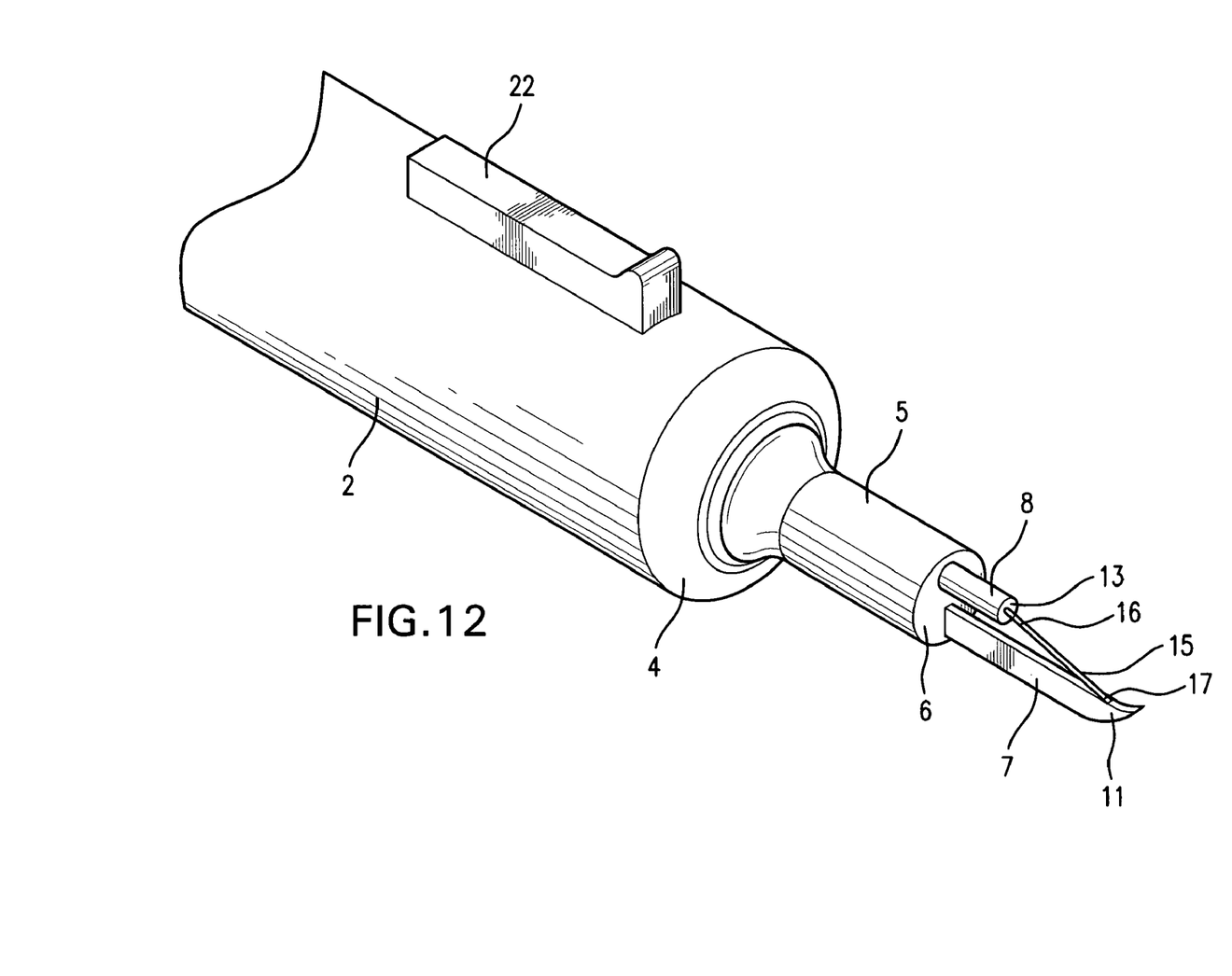
FIG. 12 is a perspective view of an alternate embodiment of the distal end of the device of FIG. 1.
Figure 13:
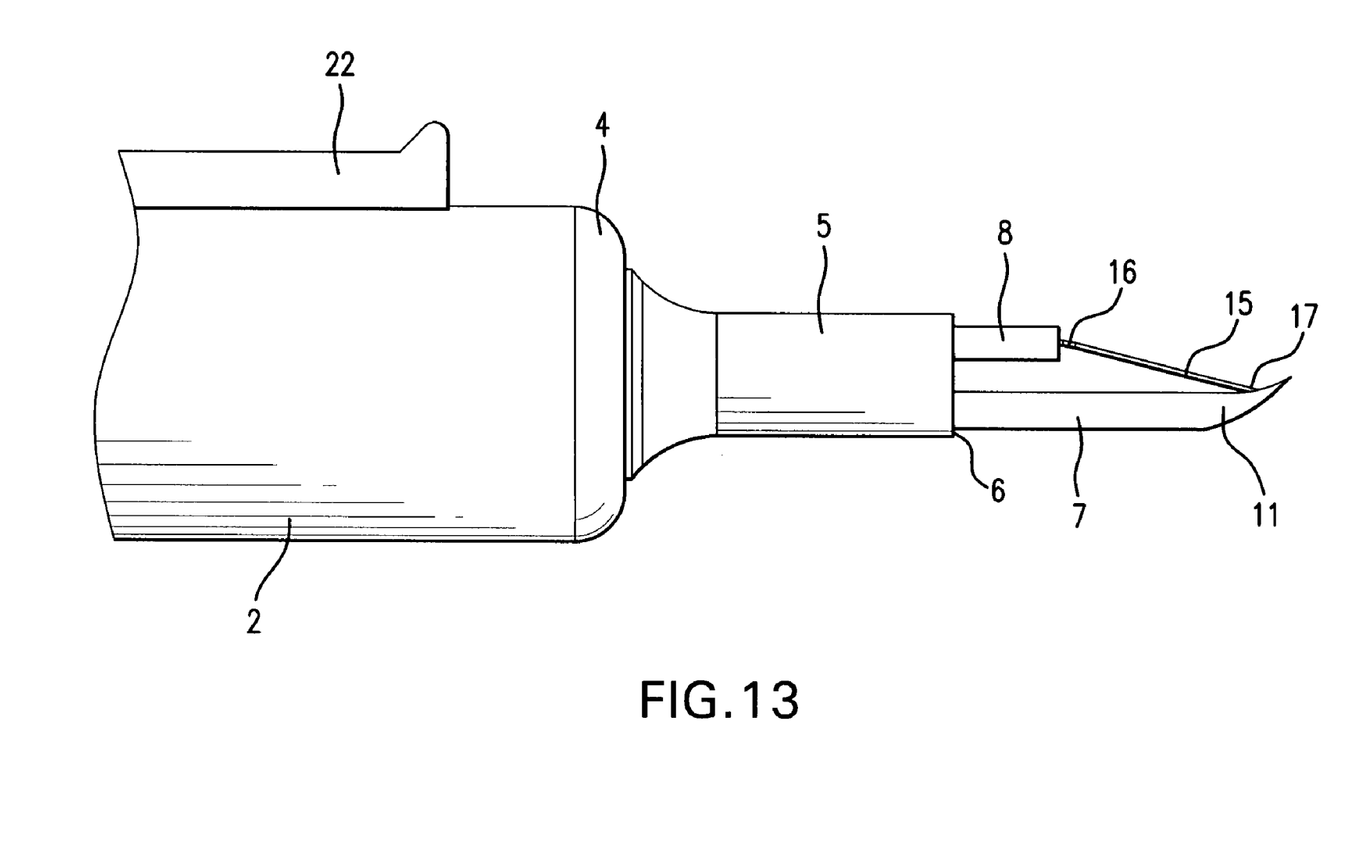
FIG. 13 is a side view of the alternate embodiment of FIG. 12.

The conductive member is shaped to facilitate insertion thereof into a suture loop. The tapered tip allows it to gently slide under the loop of the suture, between the patient's skin and a knotted portion of said suture. For example, the tapered tip may comprise a conical point. See, for example, FIGS. 2 and 3. Alternatively, the tip may take the form of flat shovel or spade-shaped scoop. See, for example, FIGS. 12 and 13.

The resistive heating element is preferably a thin filament, formed from a material such as nichrome, tungsten, nickel, stainless steel or the like. The heating element preferably joins the tapered tip of the conductive member to form an acute angle with the axis of said tapered tip ranging ranges from about 5 to about 40 degrees.

The power source required to heat the resistive heating element may be carried by the suture removal instrument itself. For example, in a preferred embodiment, the power source comprises one or more batteries contained within the elongated body. Alternatively, the elongated body may be fitted with a standard power cord and connector adapted for use with a conventional wall outlet.

The conduction means for supplying power (typically electrical power) to the heating element may take any suitable form. Examples of suitable conduction means include, but are not limited to, wires, conductive structural components, electrodeposited metal coatings and the like.

The activation means for controlling the supply of power to the heating element may take any suitable form. Examples of a suitable activation means include, but are not limited to, an actuator button, an on/off switch, and a foot pedal.

The suture removal instrument optionally includes a second conductive member placed between the insulated portion of the elongated body and the resistive heating element. The second conductive member preferably extends from the insulated distal portion of the elongated body and is disposed next to the first conductive member in a parallel fashion. In operation, one of the conductive members is connected to one side of the power source (e.g., a battery) and the other is connected to the opposite side of the power source so as to form a complete current path. The activation means can be placed anywhere along the current path. The conductive members do not heat up because they have a much larger cross-sectional area than the resistive heating element.

In a particularly preferred embodiment, the suture removal instrument comprises an elongated body having a proximal handle portion and an insulated distal portion. The handle portion contains a power source and an activation button. An insulated portion protrudes from the distal end of the proximal handle portion. First and second conductive members protrude distally from the insulated portion. It is conceivable that the heating filament could be integral with the conductive members, or that a single conductive member could be used, with the proximal end of the heating filament being connected directly to conduction means contained within the insulated portion of the elongated body.

In a preferred embodiment, the first conductive member is longer than the second conductive member and has a tapered distal end. Both the conductive members are preferably formed from an easily machined metallic material, such as brass or stainless steel, and should have good thermal conduction properties. Both the members have a coplanar axis with each other and with the proximal handle portion. The distal end of the second element is affixed to the tapered distal end of the first elongated member by a thin resistive heating element. The thin resistive heating element forms an acute angle of about 5 to 40 degrees with the axis of the first elongated member. The first and second conductive members are connected to the power source and the activation button by a suitable conduction means discussed above. Because the conductive members have much larger cross-sections than the thin resistive heating element, the conductive members are not heated by the current. Because the element is energized for only a short period of time, heating of the conductive members by the filament is minimal.

In another embodiment, intended for cutting very heavy sutures, a thermal shield, formed from a suitable plastic, ceramic or other insulating material, surrounds at least a portion of the tapered distal tip which is slipped into the suture loop, so as to prevent contact between the heated elements and the patient. Cutting very heavy suture may require that the resistive heating element be energized for longer periods of time or heated to higher temperatures and slight heating of the first and second conductive members may occur.

These and other objects and features of the invention will become more fully apparent when the following detailed description is read in conjunction with the accompanying figures and examples.

DETAILED DESCRIPTION OF THE PREFERRED EMBODIMENTS

In the context of the present invention, the following definitions apply:

The term "suture" is used to refer both to the fine thread or other material used surgically to close a wound or join tissues and to the stitch so formed.

The term "distal" refers to that end or portion which is situated farthest from the hand of the operator and closest to the body of the patient when the device is in use.

The term "proximal" refers to that end or portion situated closest to the hand of the operator and farthest away from the body of the patient when the device is in use.

The accompanying figures, described in detail below, illustrate aspects of the invention but are in no way intended to limit the scope of the present invention.

Figure 1:
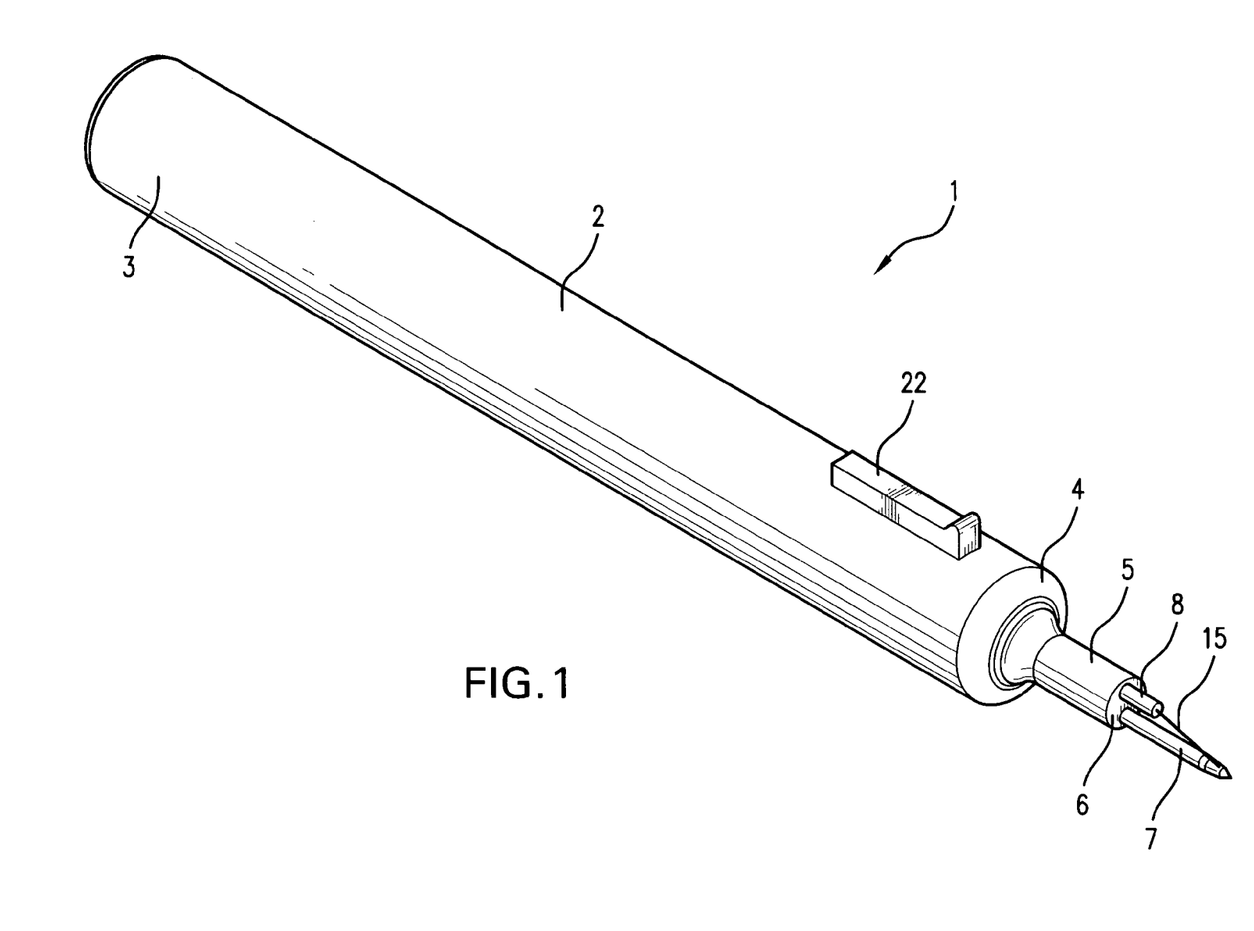
FIG. 1 is a perspective view of a thermal suture cutting device constructed in accordance with the principles of this invention.
Figure 2:
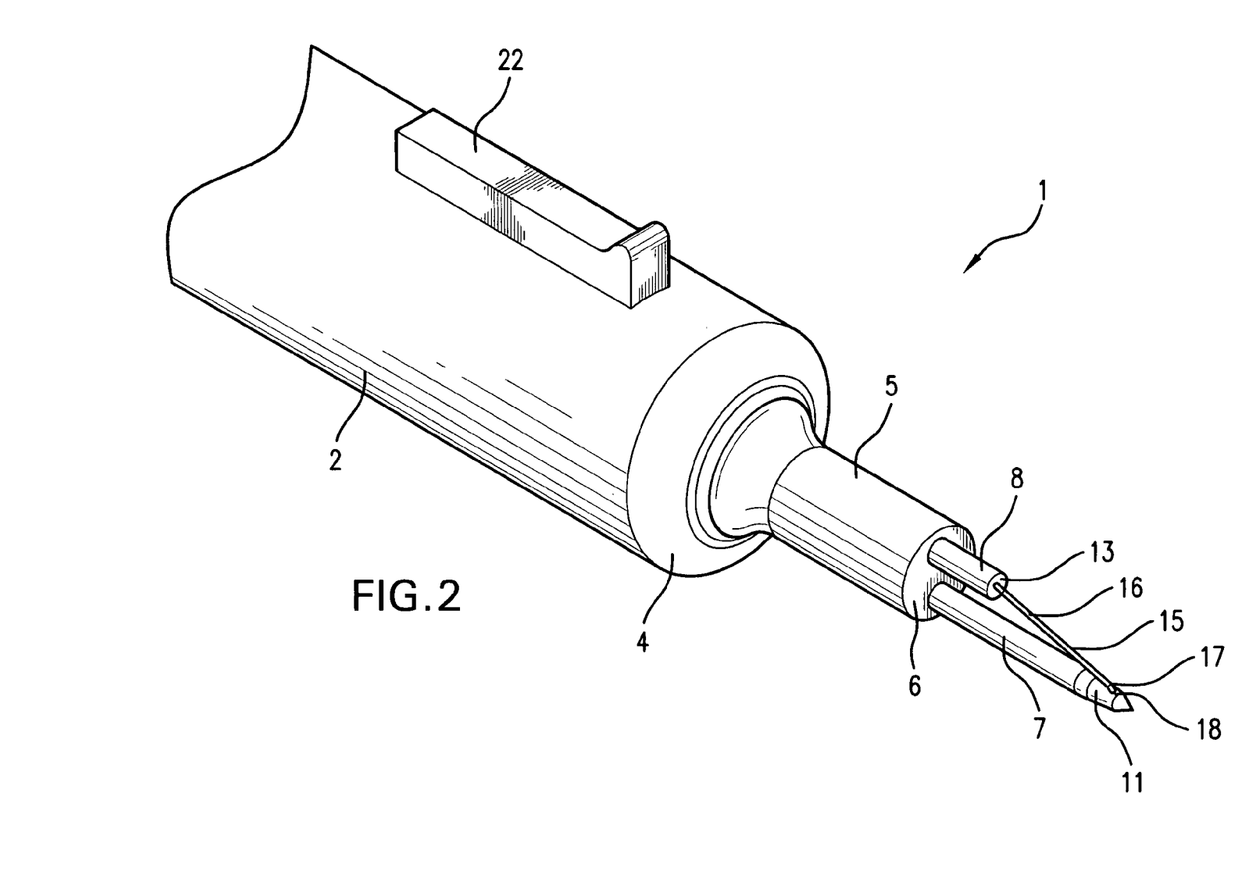
FIG. 2 is an expanded view of the distal portion of the object of FIG. 1.
Figure 3:
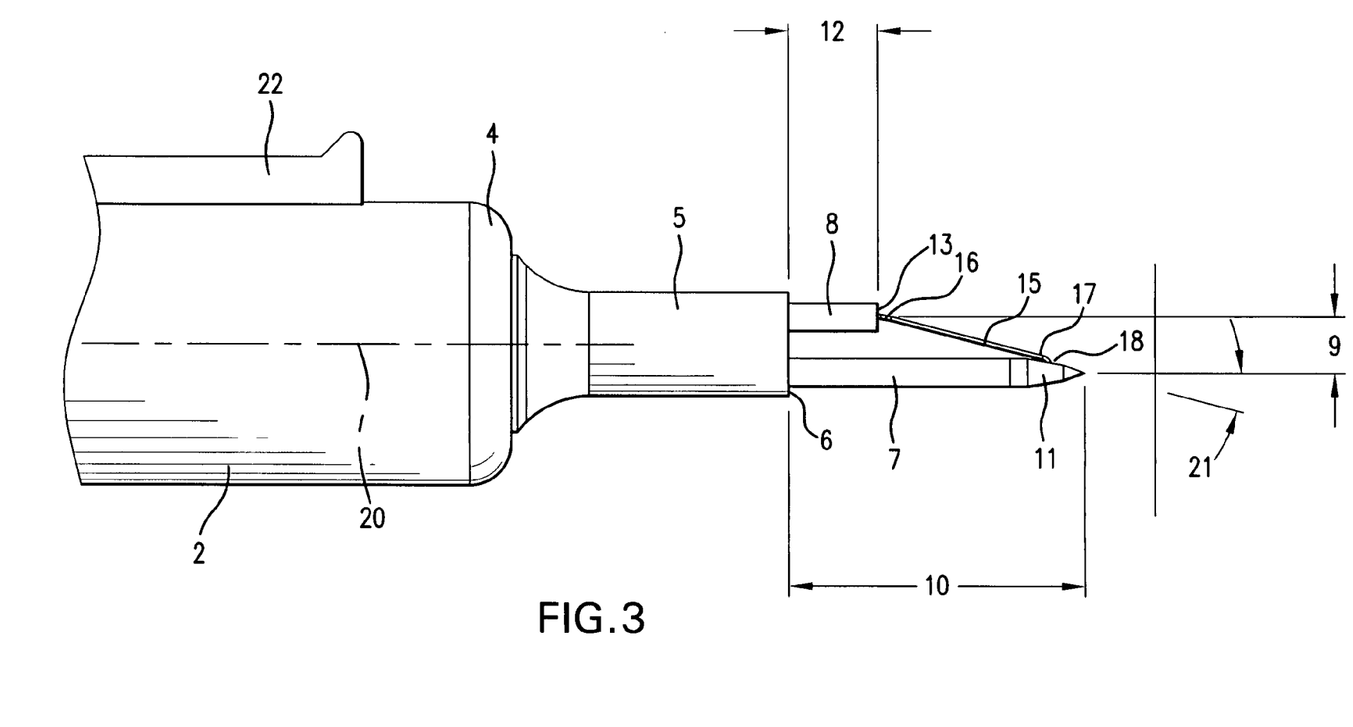
FIG. 3 is an expanded side elevation view of the distal portion of the device of FIG. 1.

Referring to FIGS. 1 through 3, thermal suture remover 1 has an elongated cylindrical body portion 2 having a proximal end 3 and a distal end 4, the elongated sections forming a handle and containing therein at least one battery. Insulator piece 5, made from a suitable plastic or ceramic dielectric material, protrudes from distal end 4 and has a distal-most surface 6, from which protrudes a first elongated rigid conductive piece 7 and a second elongated rigid conductive piece 8, pieces 7 and 8 being separated by distance 9. Elongated piece 7, protruding distance 10, has a tapered distal region 11. Elongated piece 8, protruding distance 12, has a distal end 13. Proximal end 16 of heating element 15, is affixed to distal end 13 of elongated piece 8, and distal end 17 of heating element 15 is affixed to the top surface 18 of tapered distal region 11 of elongated piece 7 such that the axes of pieces 7, 8 and 15 are coplanar. Heating element 15 is inclined to axis 20 angle 21 determined by the difference between distances 10 and 12, and distance 9. Depressing button 22 connects conductive pieces 7 and 8 to the at least one battery by a suitable conduction means, such wires, conductive structural components, electrodeposited metal coatings or the like.

Figure 4:
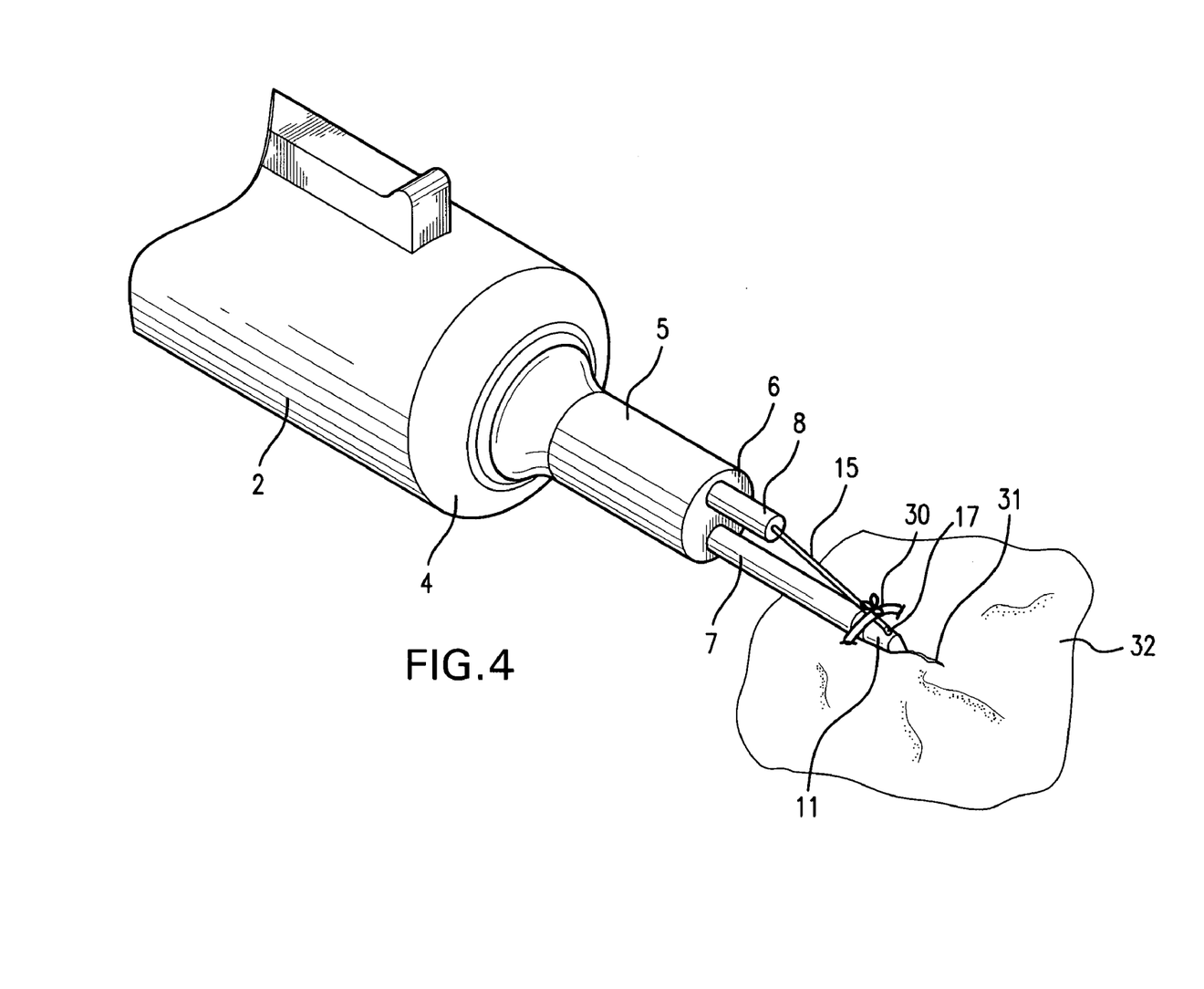
FIG. 4 is a perspective view of the device of FIG. 1 during use.
Figure 5:
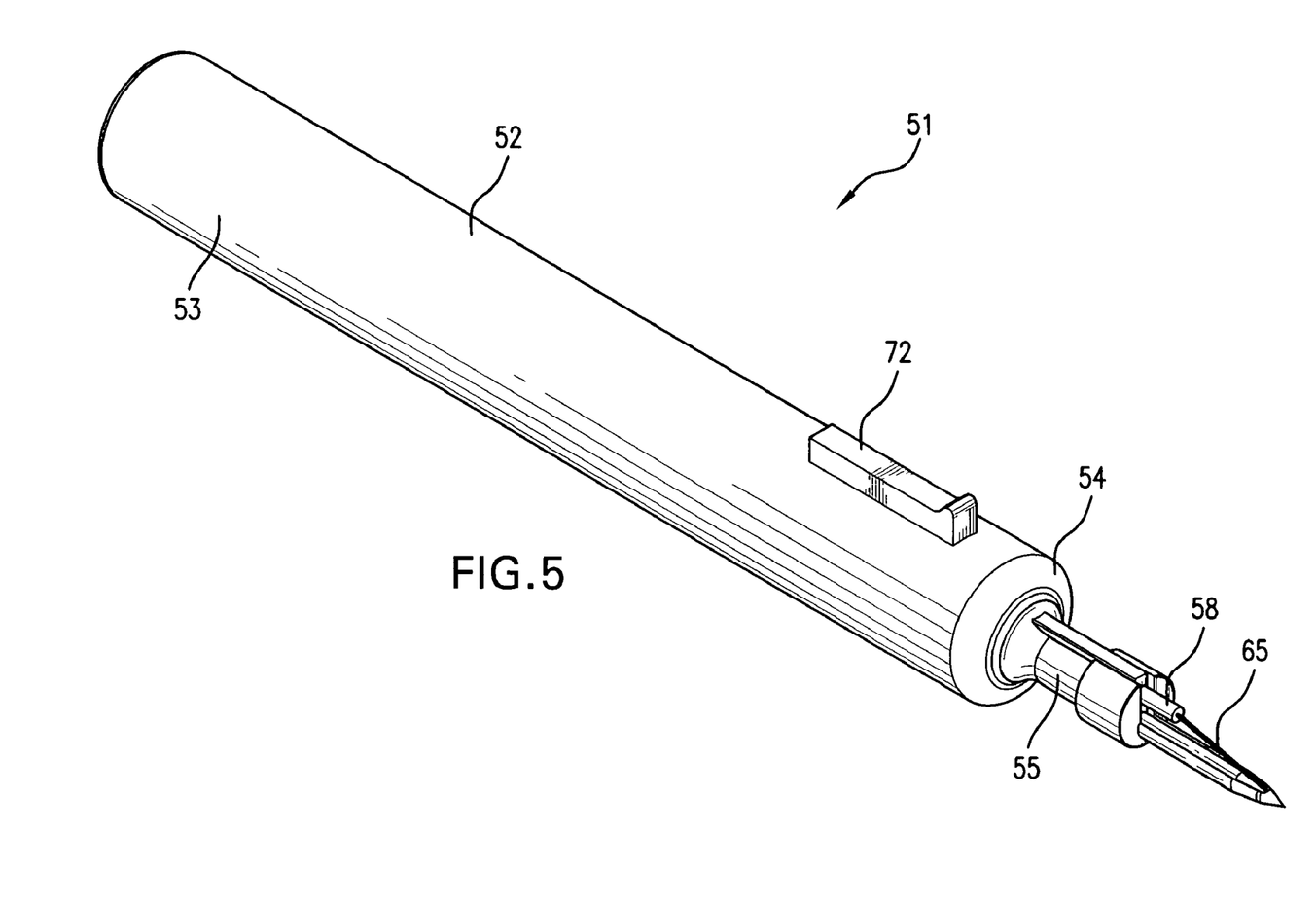
FIG. 5 is a perspective view of an alternate embodiment of the thermal suture cutting device, including a thermal shield.

As seen in FIG. 4, showing a wound 31 in tissue 32 closed by stitch 30, when removing a stitch, tapered distal portion 11 of conductive piece 7 is inserted into the loop formed by suture 30, and advanced until suture 30 contacts distal end 17 of heating filament 15. Insertion of the conductive piece may be aided by grasping the knot of the stitch with forceps and lifting slightly. Power is supplied to heating filament 15 for a brief period so as to heat filament 15. The portion of suture 30 in contact with heated filament 15 then melts and ruptures. Thereafter, the suture is removed from the skin in the usual manner. Because heating filament 15 is energized for only a brief time, and because conductive pieces 7 and 8 have a relatively larger thermal mass and cross-sectional area as compared to heating filament 15, conductive pieces 7 and 8 do not heat sufficiently to cause patient discomfort.

In another embodiment used, for instance, for, cutting very heavy suture which may require that the filament be heated for a longer time, a plastic or ceramic shield protects the patient from possible heating of the conductive piece. Referring to FIGS. 5 through 8, thermal suture remover 51 has an elongated cylindrical portion 52 having a proximal end 53 and a distal end 54, the elongated sections forming a handle and containing therein at least one battery. Protruding from distal end 54, insulator piece 55 having a cylindrical distal portion 73 of radius 74 and key 75 of width 76, and made from a suitable plastic or ceramic dielectric material, has a distal-most surface 56 from which protrude a first elongated rigid conductive piece 57 and a second elongated rigid conductive piece 58, pieces 57 and 58 being separated by distance 59. Elongated piece 57, protruding distance 60, has a tapered distal portion 61. Elongated conductive piece 58 protruding distance 62, has a distal end 63. Proximal end 66 of heating element 65 is affixed to distal end 63 of elongated conductive piece 58, and distal end 67 of heating element 65 is affixed to distal surface 68 of elongated conductive piece 57 such that the axes of pieces 57, 58 and 65 are coplanar. Heating element 65 is inclined to axis 70 angle 71, determined by the difference between distances 60 and 62, and distance 59. Depressing button 72 connects conductive pieces 57 and 58 to the at least one battery by a suitable conduction means. Thermal shield 78, made of either a suitable thermoplastic or ceramic material, surrounds elongated piece 57 and distal end 67 of heating filament 65 and mounts to insulator 55.

Figure 6:
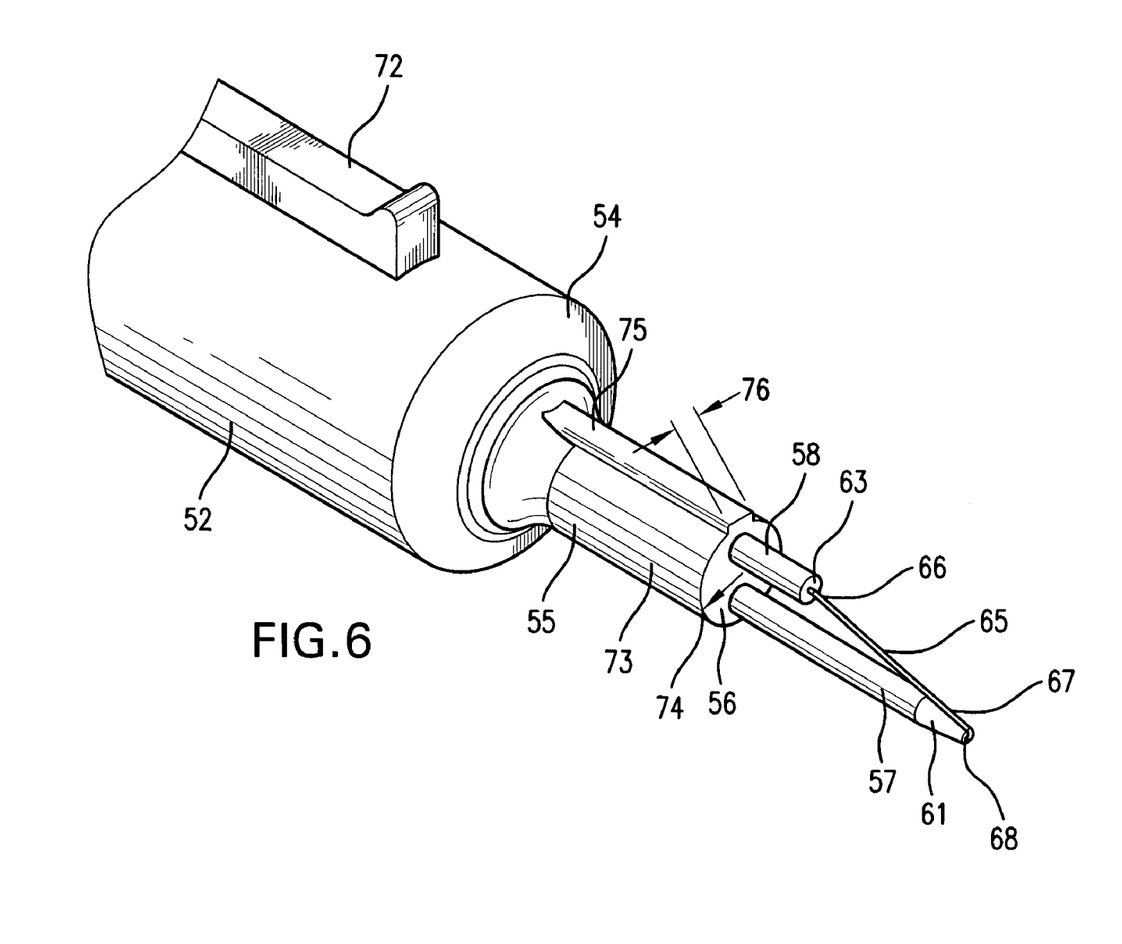
FIG. 6 is an expanded view of the distal region of the device of FIG. 5, with the thermal shield removed.
Figure 7:
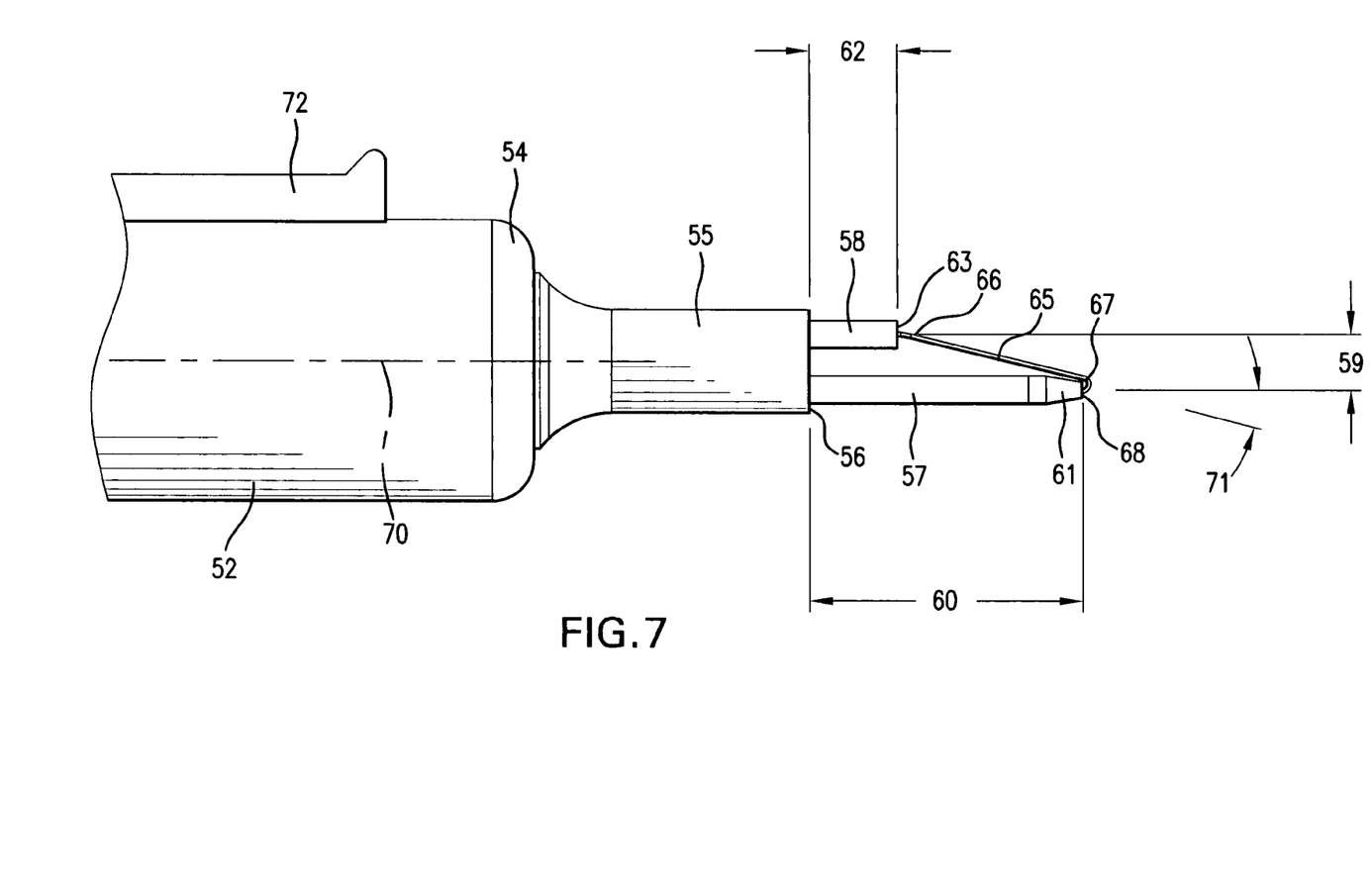
FIG. 7 is an expanded side elevation view of the device of FIG. 6.
Figure 8:
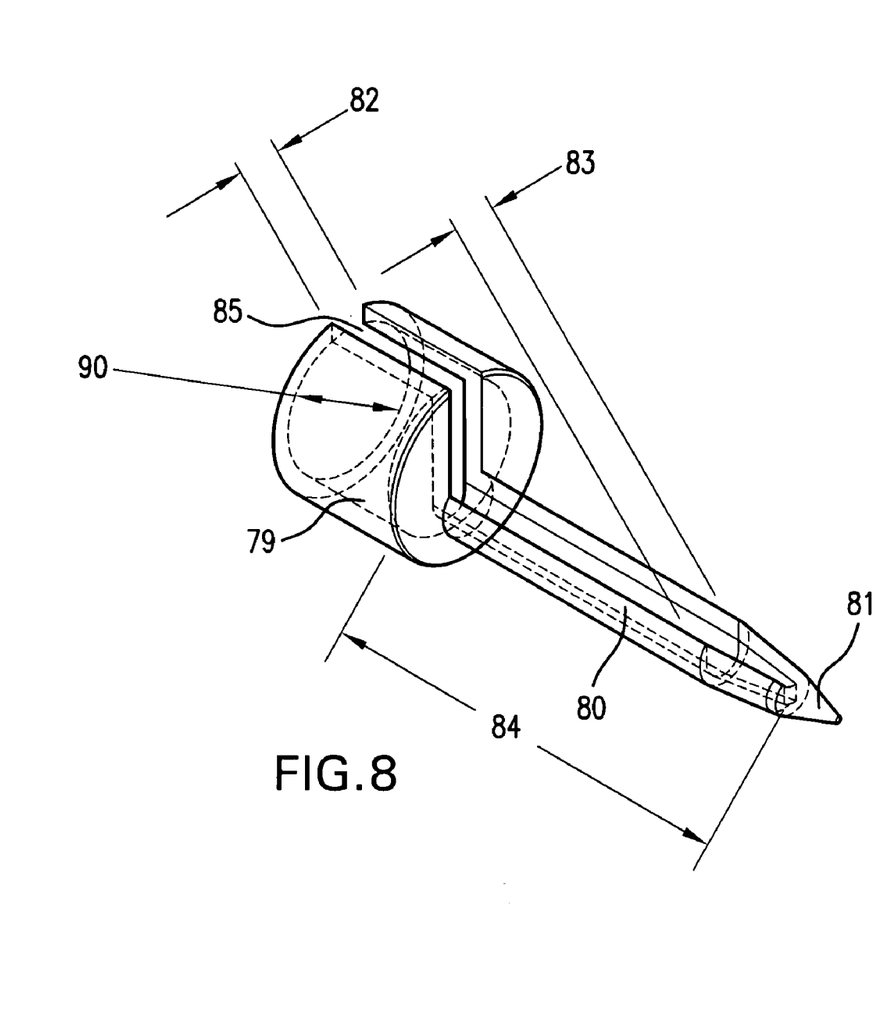
FIG. 8 is a perspective view of the thermal shield of the device of FIG. 5.

Referring primarily to FIG. 8, but also FIG. 6, shield 78 has a tubular section 79 and a U-shaped channel portion 80 having a closed, tapered, distal end 81. Tubular section 79 has an inner diameter 90 approximately equal to twice radius 74 (see FIG. 6) of cylindrical portion 73 of insulator 55, and an axial slot 85 of width 82 slightly greater than width 76 of key 75. The inner width 83 of channel portion 80 is slightly greater than the diameter of elongated piece 57, and length 84 of channel portion 80 is slightly greater than length 60 of piece 57. Shield 78 is preferably made from a suitable polymeric or ceramic material.

Figure 9:
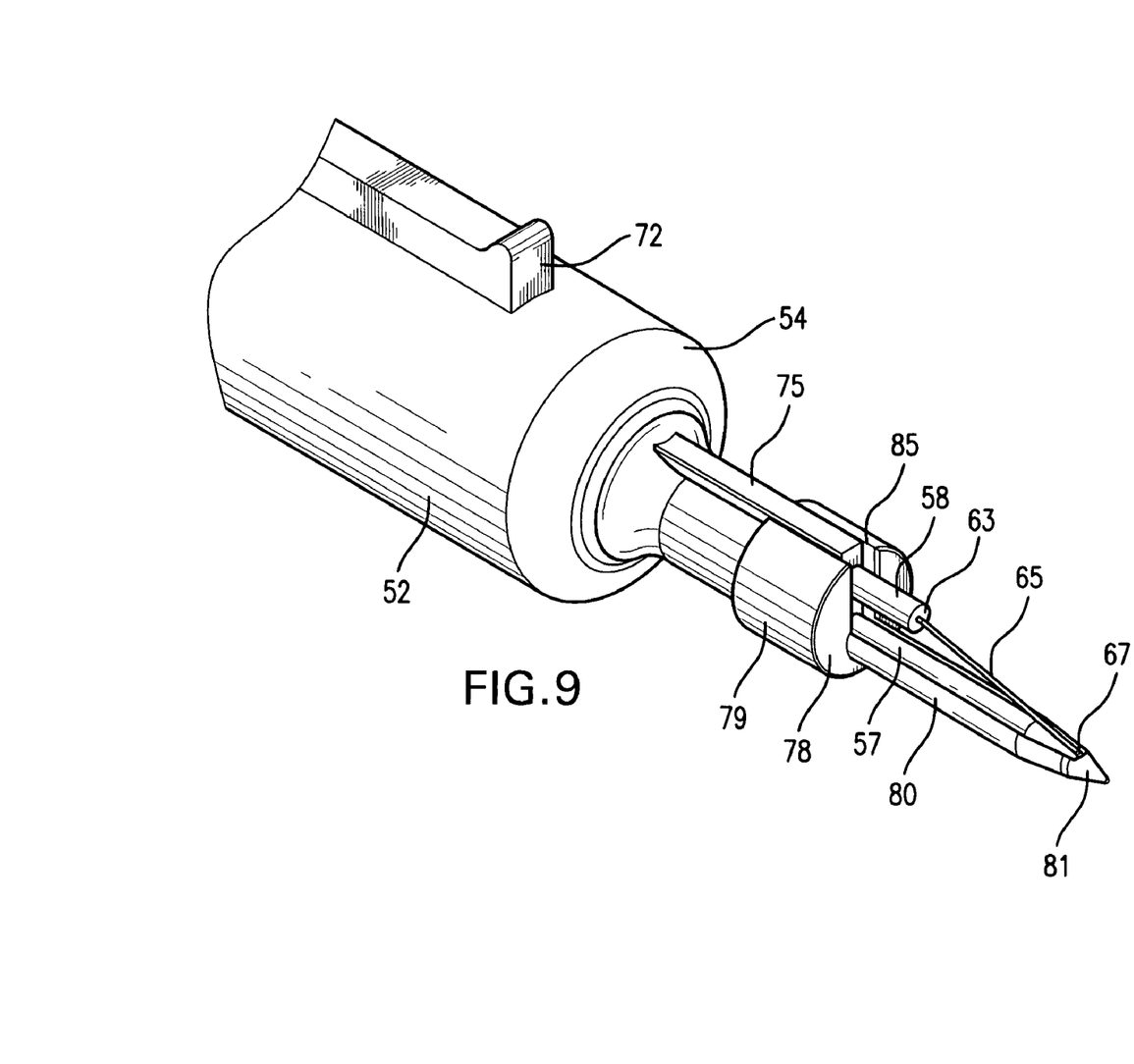
FIG. 9 is an expanded perspective view of the distal region of the device of FIG. 5.
Figure 10:
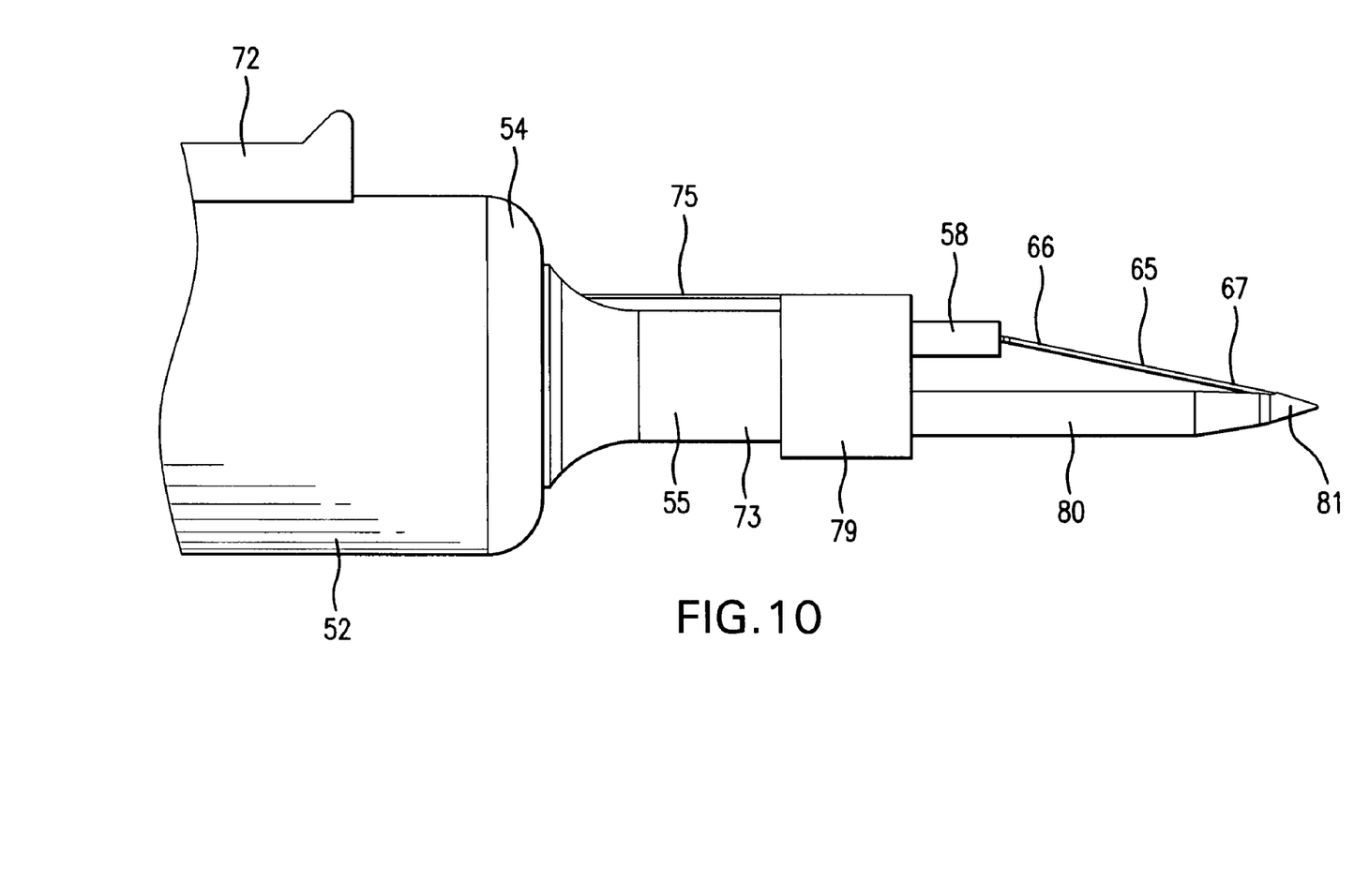
FIG. 10 is an expanded side elevation view of the distal region of the device of FIG. 5.

Referring to FIGS. 9 and 10, shield 78 is assembled to insulator 55, the tubular portion 79 of shield 78 being affixed to cylindrical portion 73 of insulator 55 and alignment being established by key 75 of insulator 55 and slot 85 of shield 78. Channel portion 80 of shield 78 surrounds elongated piece 57 such that distal end 67 of filament 65 is recessed within the channel.

Figure 11:
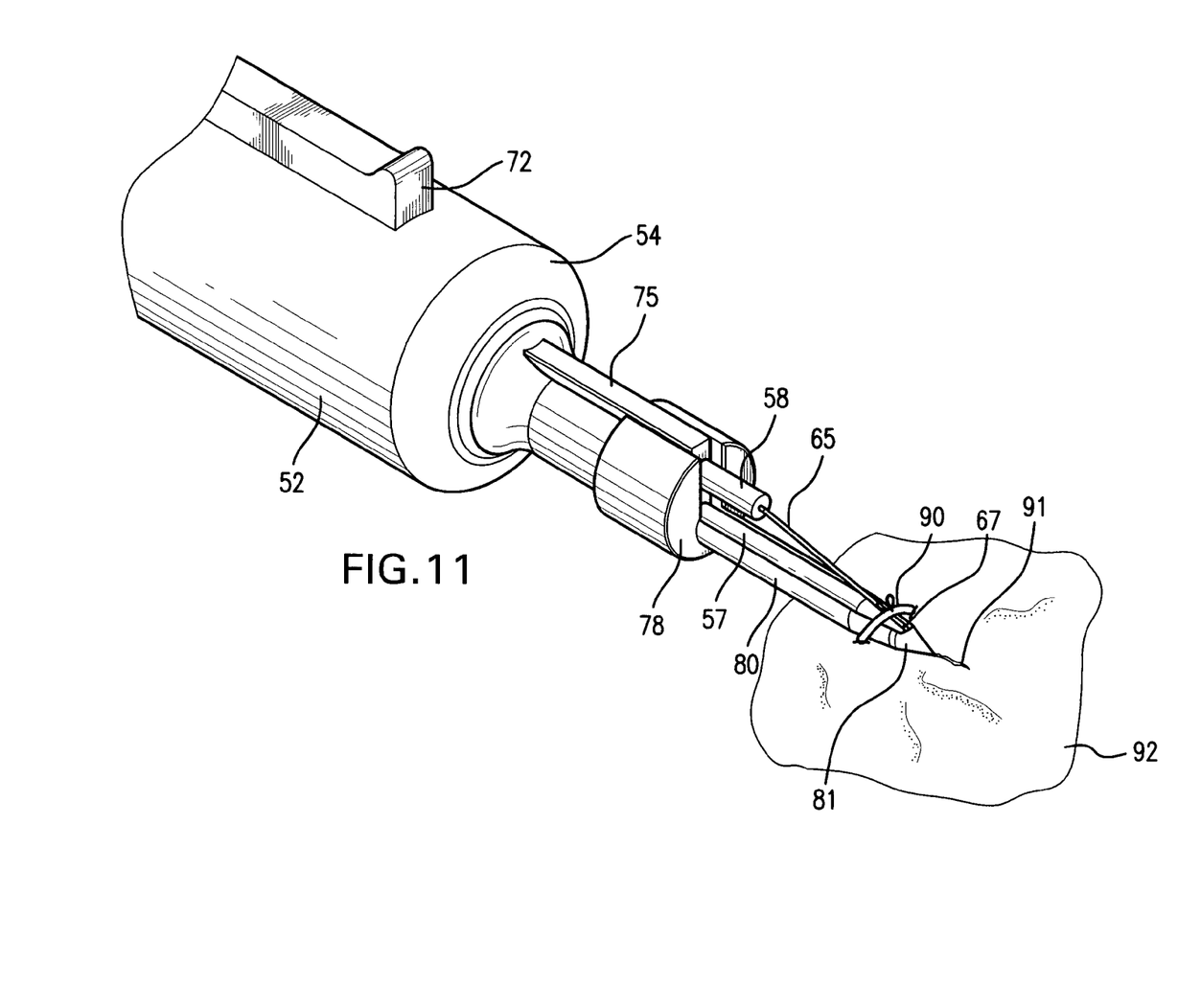
FIG. 11 is a perspective view of the device of FIG. 5 during use.

Referring to FIG. 11, showing a wound 91 in tissue 92 closed by suture 90, when removing a stitch, tapered distal portion 81 of shield 80 is inserted into the loop formed by suture 90, and advanced until suture 90 contacts distal end 67 of filament 65. Insertion of the shield 80 may be aided by grasping the knot of the stitch with forceps and lifting slightly. Power is supplied to filament 65 for a brief period so as to heat filament 65 and the portion of suture 90 in contact with filament 65 causing suture 90 to melt and rupture. Thereafter the suture is pulled from the skin in the usual manner. Shield 80 prevents heat from elongated piece 57 from reaching the patient.

The disclosure of each publication, patent or patent application mentioned in this specification is specifically incorporated by reference herein in its entirety.

The invention has been illustrated by reference to specific examples and preferred embodiments. However, it should be understood that the invention is intended not to be limited by the foregoing description, but to be defined by the appended claims and their equivalents.

What is claimed:

1. A suture removal instrument comprising:
   (a) an elongated body having a proximal handle portion and insulated distal portion;
   (b) a first conductive member extending from the insulated distal portion of said elongated body in a parallel fashion, being substantially straight along their respective longitudinal axes, said first conductive member terminating in a tapered tip;
   (c) a resistive heating element extending in a linear fashion between said first and second conductive members, wherein said resistive heating element is affixed at its proximal end to the distal end of said second conductive member and at its distal end to said tapered tip of said first condnctive member such that said resistive heating element forms an acute angle with the longitudinal axis of said first conductive member, said angle dictated by the respective lengths of the conductive members and the spacing there between;
   (d) conduction means for supplying power to said heating element; and
   (e) activation means for controlling the supply of power to said heating element.

2. The suture removal instrument of claim 1, wherein said elongated body comprises a cylindrical housing.

3. The suture removal instrument of claim 1, wherein said first conductive member comprises an elongated cylinder.

4. The suture removal instrument of claim 1, wherein said tapered tip comprises a conical point.

5. The suture removal instrument of claim 1, wherein said tapered tip comprises a flat scoop.

6. The suture removal instrument of claim 1, wherein said resistive heating element comprises a thin filament.

7. The instrument of claim 1, wherein said resistive heating element is formed from a material selected from the group consisting of nichrome, tungsten, nickel, and stainless steel.

8. The suture removal instrument of claim 1, wherein said acute angle ranges from about 5 to about 40 degrees.

9. The suture removal instrument of claim 1, wherein said instrument further comprises a power source contained within the handle portion of said elongated body.

10. The suture removal instrument of claim 9, wherein said power source comprises at least one battery.

11. The suture removal instrument of claim 1, wherein said instrument further comprises a power cord adapted for connection to a wall outlet extending from said elongated body.

12. The suture removal instrument of claim 1, wherein said activation means for controlling the supply of power to said heating element comprises an actuator button.

13. The suture removal instrument of claim 1, further comprising a thermal shield disposed about said first conductive member and mounted to the insulated portion of said elongated body.

14. The suture removal instrument of claim 13, wherein said thermal shield comprises a tubular section and a U-shaped channel portion having closed, tapered distal end, wherein said tubular section is friction fit to said insulated portion and the tapered tip of said first conductive member fits snugly within said U-shaped channel portion.

15. The suture removal instrument of claim 14, wherein said thermal shield is secured to the insulated portion of said elongated body via mating slot and key elements.

16. A method for removing a suture from the skin of a patient, comprising the steps of:
 (a) inserting the resistive heating element of the suture removal instrument of claim 1 under a loop of the suture, between the patient's skin and a knotted portion of said suture;
 (b) activating the resistive heating element so as to heat and cut the suture loop, and
 (c) removing the suture from the patient's skin.

* * * * *

UNITED STATES PATENT AND TRADEMARK OFFICE
CERTIFICATE OF CORRECTION

| | |
|---|---|
| PATENT NO. | : 7,048,746 B2 |
| APPLICATION NO. | : 10/600368 |
| DATED | : May 23, 2006 |
| INVENTOR(S) | : Warden et al. |

It is certified that error appears in the above-identified patent and that said Letters Patent is hereby corrected as shown below:

In the specification, column 6, line 23 (claim 1, line 4), please change "a first conductive member" to -- first and second conductive members --.

Signed and Sealed this

Twelfth Day of September, 2006

JON W. DUDAS
*Director of the United States Patent and Trademark Office*